(12) United States Patent
Ou-Yang et al.

(10) Patent No.: US 8,537,356 B2
(45) Date of Patent: Sep. 17, 2013

(54) OPTO-FLUIDIC NANOPARTICLE DETECTION APPARATUS

(75) Inventors: H. Daniel Ou-Yang, Bethlehem, PA (US); Xuanhong Cheng, Bethlehem, PA (US)

(73) Assignee: Lehigh University, Bethlehem, PA (US)

(*) Notice: Subject to any disclaimer, the term of this patent is extended or adjusted under 35 U.S.C. 154(b) by 306 days.

(21) Appl. No.: 12/920,262

(22) PCT Filed: Mar. 2, 2009

(86) PCT No.: PCT/US2009/035683
§ 371 (c)(1),
(2), (4) Date: Jan. 3, 2011

(87) PCT Pub. No.: WO2009/108921
PCT Pub. Date: Sep. 3, 2009

(65) Prior Publication Data
US 2011/0085166 A1    Apr. 14, 2011

Related U.S. Application Data

(60) Provisional application No. 61/032,184, filed on Feb. 28, 2008.

(51) Int. Cl.
*G01N 21/00* (2006.01)
(52) U.S. Cl.
USPC ........... 356/338; 356/300; 356/344; 356/369; 250/225

(58) Field of Classification Search
USPC ............... 356/300–334, 338, 369; 250/225
See application file for complete search history.

(56) References Cited

U.S. PATENT DOCUMENTS

| | | | |
|---|---|---|---|
| 5,198,369 A * | 3/1993 | Itoh et al. ................ | 436/534 |
| 5,283,417 A * | 2/1994 | Misawa et al. .......... | 219/121.85 |
| 6,677,566 B2 * | 1/2004 | Knebel et al. ............ | 250/201.3 |
| 7,071,006 B2 * | 7/2006 | Tajima et al. ............ | 436/526 |
| 7,622,710 B2 * | 11/2009 | Gluckstad ................ | 250/251 |
| 2005/0146718 A1 * | 7/2005 | Bustamante et al. ..... | 356/338 |

* cited by examiner

*Primary Examiner* — Gregory J Toatley
*Assistant Examiner* — Isiaka Akanbi
(74) *Attorney, Agent, or Firm* — Kurt Ehresman; Rhoads & Sinon LLP (57) ABSTRACT

Provided herein are new methods and apparatus for quantitative measurement and analysis of particles, including new apparatus systems to process and detect nanoparticles in suspension. By focusing a laser beam at the center of a reservoir, nanoparticles are concentrated by optical energy, and fluorescent intensity at the focal point of the laser is measured to quantify particle concentration in the reservoir. The techniques may be applied to the analysis of suspensions of nanoparticles, including natural particles (e.g., microorganisms including whole viruses, bacteria, animal cells, and proteins) and synthetic particles (e.g., colloidal latexes, paints, pigments, and metallic or semiconductor nanoparticles) for medical and industrial applications, among others.

19 Claims, 7 Drawing Sheets

OPTO-FLUIDIC NANOPARTICLE DETECTION APPARATUS

CROSS-REFERENCE TO RELATED APPLICATIONS

This application claims the priority of U.S. 61/032,184, filed Feb. 28, 2008, the entire contents of which are incorporated herein by reference.

FIELD

This application describes an apparatus for use in concentrating, analyzing, and manipulating nanoparticles with an optical sensor.

BACKGROUND

Suspension of micro- and nanoparticles are ubiquitous in our environment both naturally formed, such as microorganisms, including viruses, bacteria, animal cells, proteins, etc., or synthetically manufactured, such as colloidal latexes, paints, pigments and a variety of metallic or semiconductor nanoparticles for industrial applications. The ability to control the strength of particle-to-particle interactions and the stability of the particles in suspension are critical for a variety of industries that process nanoparticles, whether as raw materials, manufacturing intermediates, or final products. One of the most important parameters during the processing of these particulate suspensions is measuring and controlling of colloidal stability against fluctuation or aggregation.

Control of suspension stability is a complex task involving parameters such as salt concentration, pH, solvent conditions, surface charge of the particles, and the type and quantity of surfactants in the solution. Most of these adjustable parameters are configured to fine tune particle-to-particle interactions. The stronger the repulsive interaction between the particles, the more stabile the suspension is. In industrial practice, in-line monitoring of colloidal stability is difficult to implement because traditional monitoring instruments are quite complex. More often, the stability of colloidal suspensions against mechanical agitation or chemical variations (e.g., pH and salt) are tested in batches where samples are removed from a reactor. In such cases, the transition from a desired stable phase to the flocculated phase can be monitored by any of visual inspection (non-homogeneous texture), light transmission, or scattering techniques (degree of opacity). However, these monitoring techniques provide limited results and represent the stability of sample that may have altered after removal from the reactor. Accordingly, a continuing and unmet need exists for new and improved methods that can be use to study nanoparticles in solution without mechanical or chemical interventions, especially nano-scale methods. Using light to create mechanical force to manipulate the physical behaviors of particles in the medium surrounding them is a desirable means for studying particle-to-particle interactions in the medium. Such parameters may be measured in situ without needing to interrupt a process or remove the solution from the batch process.

SUMMARY

Provided herein are new methods for quantitative measurement and analysis of particles, including new platforms to process and detect and measure nanoparticles in suspension, preferably in situ. By focusing a laser beam at the center of a reservoir, nanoparticles are concentrated by optical energy, and fluorescent intensity at the focal point of the laser is measured to quantify particle concentration in the reservoir. Such methods may be applied to the analysis of suspensions of nanoparticles, including natural particles (e.g., microorganisms including whole viruses, bacteria, animal cells, and proteins), as well as synthetic particles (e.g., colloidal latexes, paints, pigments, and metallic or semiconductor nanoparticles). The methods are suitable for industrial application, as well as personal services, such as medical testing.

In the methods described herein, light is used to locally confine and spatially concentrate nanoparticles for potential applications in chemical and biological separation and detection, as well as technologies relating to nanoparticles that are used in coatings, pigments, food, beverages, drugs and cosmetics, among others. For example, light may be used to concentrate nanoparticles in situ wherein the optical trapping volume is much larger than the particles, effectively producing an optical bottle to confine, concentrate and manipulate the nanoparticles in a region of about 5-100 $\mu m^3$.

Since the inception of optical trapping technologies (some times known as "optical tweezers"), there has been a rapid advance in the technology, such as using focused laser light to manipulate single particles. Provided herein are heretofore unknown methods of using focused laser beams to manipulate multiple nanoparticles in a single trapping volume. Thus, the inventors have expanded optical trapping from utility in studying single particles to trapping of multiple nano-sized objects. Such methods may be advantageously exploited in nano-fabrication technology and biotechnology, for example, in controlling the interactions between colloids, and detecting viral loads (i.e., viral particles) in diluted samples of blood.

Accordingly, new methods to process, trap, and measure particles in suspension are described herein. The methods are based on the application of highly concentrated light to manipulate particle concentration in a suspension within a highly localized area. For example, colloidal stability can be reliably monitored by measuring the degree of concentration change in response to the applied light intensity as a quantitative measure of the osmotic compressibility of the suspension. The light concentration can be achieved by a variety of means including but not limited to focusing of free space light by optical lenses; focusing light at the tip of a single optical fiber or multiple fiber assemblies; or by taking advantage of the plasmonic resonance-enhanced near-field light concentration in the vicinity of structured metallic surfaces. The local particle concentration can be monitored by standard fluorescence detection (for labeled or naturally fluorescent particles) or by Raman or other scattering techniques (especially for label-free particles).

Additional features may be understood by referring to the accompanying Drawings, which should be read in conjunction with the following Detailed Description and Examples.

DETAILED DESCRIPTION

Optical tweezers have heretofore been used to study interparticle forces, but they have been limited to trapping micron-size individual particles at infinite dilution. Described herein is a new approach to investigate the interactions of multiple sub-micron particles in suspensions (whether native or synthetic) using a novel optical trap. Using a blinking optical trap and confocal detection of optical signals, the interactions may be measured in suspensions of colloidal particles in the range of tens to hundreds nanometers in diameter. The method can also be used to monitor "optically thick" (semi-opaque) samples by optical means to monitor the interactions of the particles in their normal processing environment using highly localized light. This diagnostic method does not require the light to penetrate deeply into the specimen.

Also provided herein are new methods for quantitative measurement of particles in solution, including new platforms to process and detect fluorescent nanoparticles in suspension. By focusing a laser beam at the center of a reservoir, nanoparticles are concentrated by optical energy, and the fluorescent intensity at the focal point of the laser is measured to quantify particle concentration in the reservoir. In an example embodiment described in detail herein below, nanoparticles (e.g., whole viruses) are first purified and concentrated (based on their sizes) through nanoporous and microporous filter membranes packaged in microfluidic devices (e.g., chips). The devices can also be used to label the nanoparticles, such as diffusing fluorescent affinity tags through the nanoporous membranes to attach to the nanoparticles. The number of viral particles is measured, and a viral load is calculated based on that measurement.

Using such methods, one can monitor the stability of particles in the size range of a few nanometers to micron size. As used herein, the term "nanoparticles" includes any particles generally having a maximum diameter in the range of about 10 nm to about 200 nm, although in principle "nanoparticles" may also include any particles having a maximum diameter smaller than the wavelength(s) of the laser light source(s). Exemplary nanoparticles include materials such as proteins, liposomes and lipid vesicles, viral particles, carbon nanotubes, pigments, latex particles, gold, silver and other metallic particles, quantum dots and other semi-conducting particles.

Figure 1:
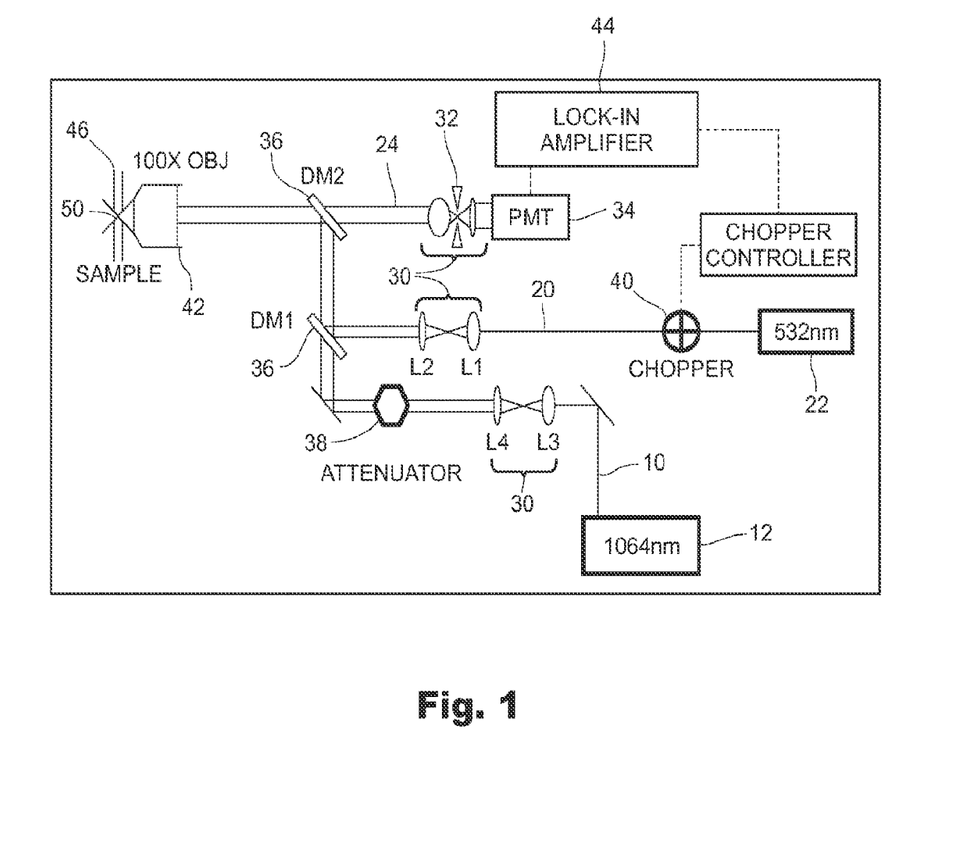
FIGS. 1, 2, 5, and 7 each schematically illustrate an opto-fluidic nanoparticle detection apparatus in accordance with an embodiment as described herein.

In an example embodiment, two co-linear lasers of different frequencies (e.g., red and green light) are beamed into a suspension of nanoparticles at an elliptical focal point whereupon the nanoparticles become physically trapped. Referring to the attached Drawings, an example optical trapping and fluorescence intensity detection apparatus is illustrated in FIG. 1. As illustrated, a confocal fluorescence intensity detection apparatus is used to measure particle concentration in an optical trap as a function of the laser intensity. In this example, fluorescently labeled particles are used as model systems, the number density of the particles being determined from the calibrated fluorescence intensity of the particles (and the fluorescence intensity being proportional to the number of particles in the optical trap). Infrared (IR) laser 12 is used at varying intensities to pull in an increasing number of fluorescent particles into focal region 50 of IR beam 10. Less intense green laser beam 20 (532 nm), aligned co-linearly with stronger IR (1064 nm) laser beam 10, is used as the fluorescence excitation light. Fluorescence signals 24 from the particles at common confocal point 50 of the two laser beams (which should ideally be as tight as possible) is collected by the same high N.A. microscope objective lens 42 that produced common focal point 50 in the sample.

Still referring to FIG. 1, fluorescence light 24 passes through pinhole aperture 32 located at a point conjugated to the common laser focus before the light is collected by photomultiplier (PMT) 34. This confocal fluorescence detection scheme is employed to ensure that the detected fluorescence intensities are only from fluorescence signals 24 originating at the diffraction-limited focal region. The relationship between fluorescence signal 24 intensity and the particle number density may be derived from the conversion of the changes in fluorescence intensity to changes in particle number density. Fluorescence intensity measurements using a periodically chopped probe laser beam in conjunction with lock-in detection are employed to improve the signal to noise ratio in order to accurately detect the changes in particle density.

Figure 2:
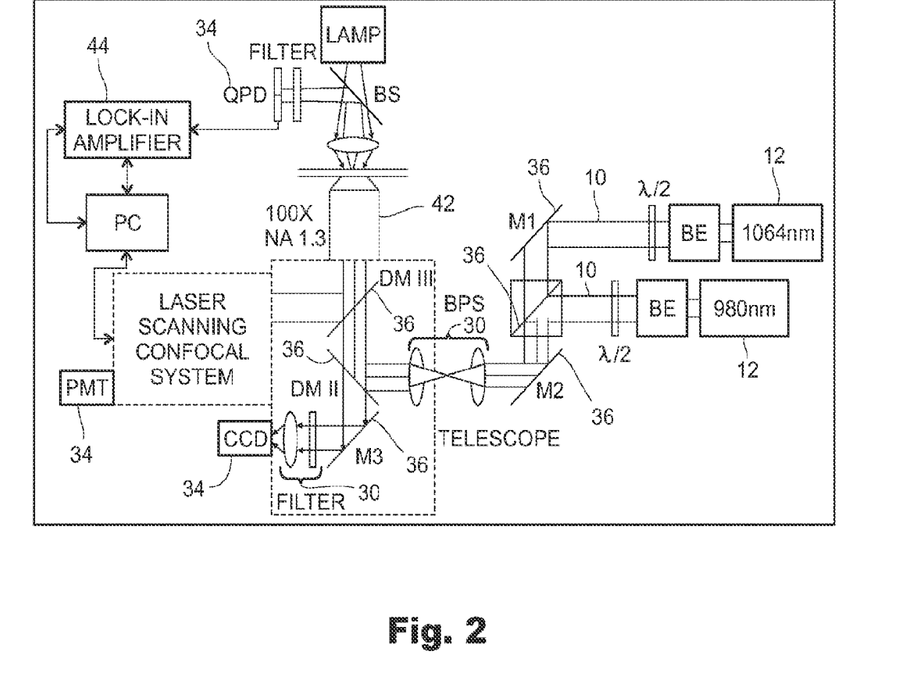

FIG. 2 illustrates an embodiment in which optical trapping is combined with a commercial confocal laser scanning microscope (e.g., Olympus Fluo-View FV-1000) to image particle distribution profiles in the vicinity of optical trap 50. This is done by steering IR lasers 10 (e.g., 1064 nm and/or 980 nm) into one of the ancillary input ports (right side port). The dichromatic filter is used in such a way that optical trapping IR laser beams 10 are not in conflict with the beam path of the laser scanning imaging. The use of multiple laser lines equipped with the FV-1000 (six color channels from UV or near IR) enable a broad range of fluorescent particles or particle mixtures to be investigated.

Optical trapping of particles is caused by a radiation force that is generated on individual nanoparticles by the high gradient optical field produced by a focused laser beam. According to the classical electromagnetic theory, the radiation pressure force on dielectric particles with dimensions smaller than the wavelength of the light can be expressed by $$F_{grad} = -\frac{8\pi n_1^2 a^3 z}{R^2 C} \left[\frac{n_2^2 - n_1^2}{n_2^2 + 2n_1^2}\right] I_0(z) \quad \text{Eq. 1}$$

$$F_{scat} = \frac{128\pi^5 n_1 a^6}{3\lambda^4 C} \left(\frac{n_2^2 - n_1^2}{n_2^2 + 2n_1^2}\right)^2 I_0(z) \quad \text{Eq. 2}$$

where a is the radius of the particle, c the speed of light, and $n_1$ and $n_2$ are the refractive indices of the medium and the particle, respectively. It can be shown that $F_{grad} > F_{scat}$ for $a \leq 0.2\lambda$. In this case, we assume $F_{rad} \approx F_{grad}$ and consider that the nanoparticle in a Gaussian optical field is in an effective potential energy well:

$$U(r) = -\frac{4\pi n_1^2 a^3}{c}\left[\frac{n_2^2 - n_1^2}{n_2^2 + n_1^2}\right] I_0 e^{-r^2/R^2} = -U_0 e^{-r^2/R^2} \quad \text{Eq. 3}$$

$$U_0 = \frac{4\pi n_1^2 a^3}{c}\left[\frac{n_2^2 - n_1^2}{n_2^2 + n_1^2}\right] I_0 \equiv \beta I_0 \quad \text{Eq. 4}$$

where R is the half-width of the Gaussian beam at the focal point. While one could calculate the potential energy $U_0$ (or $\beta$, the factor that determines $U_0$ for a given laser intensity $I_0$) for a nanoparticle with known index of refraction in a known distribution of light, the actual value of $\beta$ can be determined experimentally.

At low concentration, or when interactions between the nanoparticles in suspension are negligible, the osmotic pressure of a colloidal suspension with number density N can be written as $P_{osmo} = Nk_BT$ where $k_B$ is the Boltzmann constant and T the absolute temperature. Considering the excess particles in the area of the focused laser beam, the mechanical equilibrium between the radiation pressure and the osmotic pressure in this region can be described as follows:

$$-N\frac{\partial U}{\partial r} = NF_{rad} = \frac{\partial P_{osmo}}{\partial r} = \frac{\partial P_{osmo}}{\partial N}\frac{\partial N}{\partial r} \qquad \text{Eq. 5}$$

$$-N\frac{\partial U}{\partial r} = k_B T \frac{\partial N}{\partial r} \qquad \text{Eq. 6}$$

The above equation can be integrated to yield the Boltzmann distribution of the particles in a potential well due to the influence of the focused laser beam:

$$-\frac{\partial_r U}{k_B T} = \frac{dN}{N} \rightarrow N(r) = N_0 e^{-U(r)/k_B T} \qquad \text{Eq. 7}$$

For the more general case when the concentration is not low or when the interactions are not negligible, N(r) can be determined by a similar consideration of force balance. For the interest of measuring the trapping potential energy $U_0$ and $\beta$, we present here a simple analysis on how measurements of the particle concentration in the optical trap can lead to an accurate determination of $\beta$ and the osmotic compressibility of the colloidal suspension. From the definition of osmotic compressibility and the consideration of the mechanical balance between osmotic pressure and radiation pressure at the low pressure limit, we have $$\kappa_T = \frac{1}{N}\frac{\partial N}{\partial P} \approx \frac{\Delta N}{N}\frac{1}{\overline{P}} \approx \frac{\Delta N}{N}\frac{1}{\overline{P}_{rad}} \qquad \text{Eq. 8}$$

where the average radiation pressure, or the average radiation energy density, is just $$\overline{P}_{rad} \approx \tfrac{1}{2} N U_0 \qquad \text{Eq. 9}$$

with ½ introduced to account for the Gaussian profile of the laser intensity. We thus have $$\kappa_T \approx \frac{\Delta N}{N}\frac{2}{NU_0} \text{ and } \frac{\Delta N}{N} = \frac{1}{2}\kappa_T N U_0 = \frac{1}{2}\kappa_T N \beta I_0 \qquad \text{Eq. 10}$$

In order to understand how to determine the osmotic compressibility $\kappa_T$ and $\beta$ the osmotic pressure and the osmotic compressibility are expressed in terms of the virial expansion, shown below $$P_{osmo} = N(1 + B_2 N + B_3 N + \dots )k_B T \qquad \text{Eq. 11}$$

$$\kappa_T \equiv \frac{1}{N}\frac{\partial N}{\partial P_{osmo}} = \{N(1 + 2B_2 N + 3B_3 N^2 + \dots )k_B T\}^{-1} \qquad \text{Eq. 12}$$

where $B_2$ and $B_3$ are the second and third virial coefficients. At very low concentration or when interactions between particles are negligible, both $P_{osmo}$ and $\kappa_T$ are reduced to the ideal gas forms. Returning to Eq. 10, we now have $$\frac{\Delta N}{N} = \frac{1}{2}\frac{1}{(1 + 2B_2 N + 3B_3^2 N + \dots )}\frac{1}{k_B T}I_0 = \frac{1}{2}f(N)\frac{\beta}{k_B T}I_0 \qquad \text{Eq. 13}$$

$$\text{where } f(N) = \frac{1}{(1 + 2B_2 N + 3B_3 N^2 + \dots )}$$

Experimentally the initial slope of dN/N vs. $I_0$ can be measured at low laser intensity. According to Eq. 13, the inverse of the slope is $$slope^{-1} = \frac{2k_B T}{\beta}(1 + 2B_2 N + 3B_3 N^2 + \dots ) \qquad \text{Eq. 14}$$

Plotting $slope^{-1}$ as a function of N, a polynomial is fitted to the data to find $\beta$, $B_2$ and $B_3$, etc. from the experiments. From $B_2$ and $B_3$ we can readily determine the osmotic compressibility $\kappa_T$.

The foregoing theoretical framework can be conceptualized by appreciating that the relative change of the particle concentration dN/N (N being the local particle concentration) in the area of the highly concentrated light reflects a balance of radiation pressure and colloidal osmotic pressure. To illustrate the concept, assume a ball of concentrated light is created in the colloidal suspension. The intensity of the light is distributed in such a way that it is strongest at the center and becomes weaker toward the boundary. Colloidal particles in the area of the light experience a radiation force produced by the light that pushes the particles toward the center where the light is most concentrated. This force is called the light radiation force or radiation pressure.

In a stable colloidal suspension, the radiation force on the particles is balanced by an osmotic pressure in the colloidal suspension which opposes increase in local particle concentration. The stronger this opposition against increase in concentration the more stable the suspension is. The colloidal stability can be described in terms of colloidal compressibility, which is a measure of how strongly the osmotic pressure changes with the change in concentration. The lower the compressibility, meaning a small change in concentration causes a rapid increase in pressure, the higher the colloidal stability. Because the radiation pressure on an individual particle depends only on the light intensity and not on the particle concentration, under the same radiation pressure at a fixed amount of concentrated light, a more stable suspension will show a smaller change in local concentration.

A variety of light sources may be used. For example, a focused laser beam from a diode pumped Nd:YG laser (250 mW) may be used as the light source. The wavelength of that exemplary laser is 1064 nm (near IR). In principle, any tightly focused light (visible or invisible) may be usable. Light sources from lasers are more convenient because they can be tightly focused into a smaller spot than a non-laser source, thus creating a higher laser intensity and larger intensity gradient. Some non-limiting examples of other usable lasers are frequency-doubled diode pumped NdYS lasers with wavelength of 632 nm (green), 980 nm solid state fiber lasers, and Ar ion gas lasers with several wavelengths ranging from UV to green. The laser intensity can be as low as a few milliwatts for some applications.

Accordingly, in an embodiment hereof, a method for manipulating a plurality of nanoparticles includes steps of (1) providing a suspension of nanoparticles in a liquid solution within a reservoir; (2) providing a first laser beam from a first laser source and a second laser beam from a second laser source; (3) applying the first laser beam through a focusing optical element and into the reservoir to thereby establish an optical gradient and forming an optical trap within the reservoir; (4) applying the second laser beam to the optical trap to thereby produce an optical signal from the nanoparticles within the optical trap; and (5) detecting the optical signal with a photodetector.

In a typical embodiment, the optical signal produced by the nanoparticles is fluorescence. The optical signal produced by the nanoparticles may be correlated with (e.g., mathematically related to) the concentration of nanoparticles or the magnitude of a particle-to-particle interaction (e.g., the stability of a colloid). Also, a plurality of optical signals may be produced by the nanoparticles and measured at different intensities of the applied second laser beam, e.g., using a chopper. That is, the second laser source may be periodically interrupted to modulate application of the either the first laser beam or the second laser beam at a predetermined frequency.

In a preferred embodiment, the first laser source has a wavelength in the infrared region and the second laser source has a wavelength in the visible region (e.g., green or blue), and the nanoparticles have an average diameter smaller than the wavelengths of the first laser source and the second laser source. For example, the nanoparticles may have an average diameter of between about 10 nm and about 200 nm. Additionally, an example optical trap has a volume of about 5 μm³ to about 100 μm³.

In yet another embodiment, an apparatus for manipulating a plurality of nanoparticles includes (1) a first laser beam from a first laser source; (2) a second laser beam from a second laser source; (3) a reservoir in optical communication with the first laser source and the second laser source (i.e., light may travel between them); (4) a focusing optical element (e.g., one or more lenses) between the first laser source and the reservoir for establishing an optical gradient and forming an optical trap within the reservoir; and (5) an optical detector in optical communication with the reservoir for measuring an optical signal produced therein.

By way of example, the first laser source may have a wavelength of about 1064 nm (e.g., red light). Also, the second laser source may have a wavelength of about 532 nm (e.g., blue or green light). The optical detector used in the apparatus may be a photomultiplier tube (PMT) or charge-coupled device (CCD) camera. The apparatus may also include means for periodically interrupting and modulating application of the first laser beam or the second laser beam at a predetermined frequency (e.g., a chopper). The apparatus may also include means for focusing the optical signal into the optical detector, as well as means for focusing the first laser beam or the second laser beam into the reservoir (e.g., lenses). The apparatus may also include other components including light sources, confocal lenses, dichroic mirrors, beam expanders, filters, amplifiers, attenuators, and microprocessors (e.g., integrated computer systems that control operation of the apparatus).

In a particular embodiment, the apparatus includes a microfluidic device for concentrating virion particles, such as a microfluidic device that includes a filtration membrane through which virion particles freely pass and a concentration membrane that concentrates the virion particles that have passed through the filtration membrane, wherein the microfluidic device contains an optically transparent reservoir.

EXAMPLES

Example 1

Figure 3:
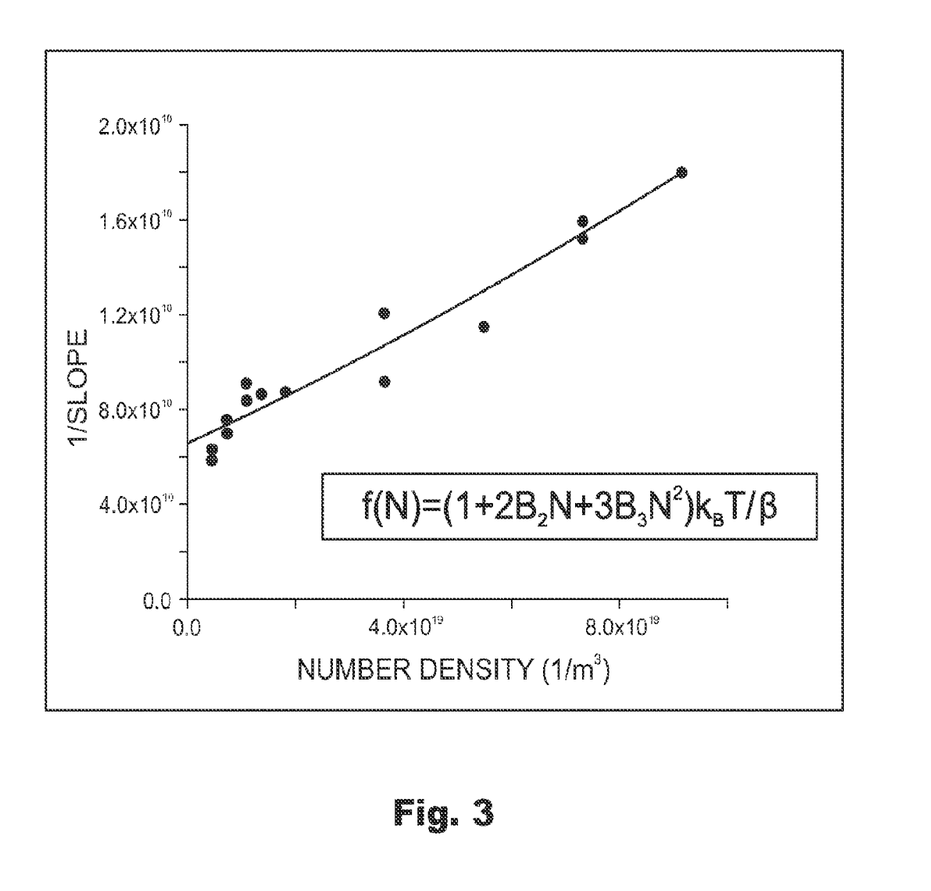
FIGS. 3 and 4 include data collected from experiments using the methods to monitor fluorescent polystyrene nanoparticles.
Figure 4:
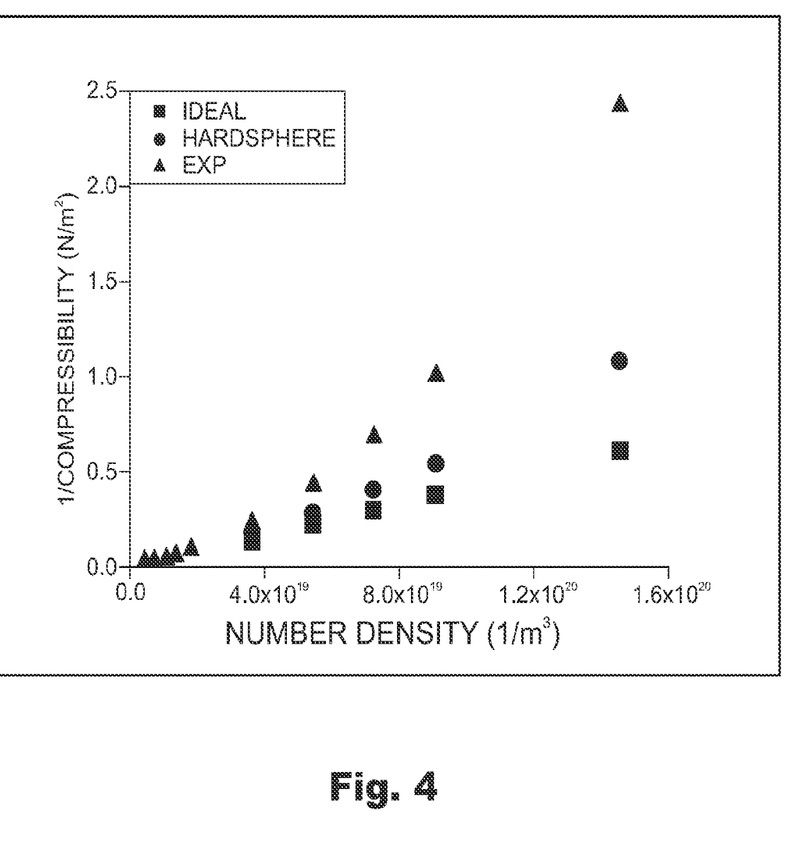

Measurement of Osmotic Compressibility of a Colloidal Suspension of Fluorescent Polystyrene Nanoparticles In accordance with the foregoing discussion, experiments were carried out on a number of fluorescent polystyrene nanoparticles of different sizes. For example, the data plotted in FIG. 3 were collected from 100 nm diameter particles with a concentration in the range of 0.1% to 8% by weight. We obtained $\beta=1.5\times10^{-10}$ $k_B Tm^2/W$, or $U_0=1.5$ $k_B T$ @ 8 mW of the laser power focused by a 1.30 N.A. objective lens to a diffraction limited spot. We also obtained $B_2=7.6\times10^{-21}$ m³ and $B_3=1.3\times10^{-41}$ m⁶, from which we can calculate the bulk modulus of the suspension at different concentrations. FIG. 4 shows a comparison of the bulk modulus for the samples, for the hard spheres with 100 nm diameter, and for the ideal gas. The trapping energies $U_0$ obtained for 63 nm and 160 nm polystyrene particles are 0.379 $k_B T$ and 8.45 $k_B T$, respectively, at 8 mW laser power under the same experimental conditions. The virial coefficients obtained are only slightly larger than the corresponding hard sphere values, which is consistent with the presence of residual salt ions in the media either from the stock solutions or from the dilution procedures.

Example 2

Measurement of Concentration of Suspended Fluorescent Polystyrene Nanoparticles

Figure 5:
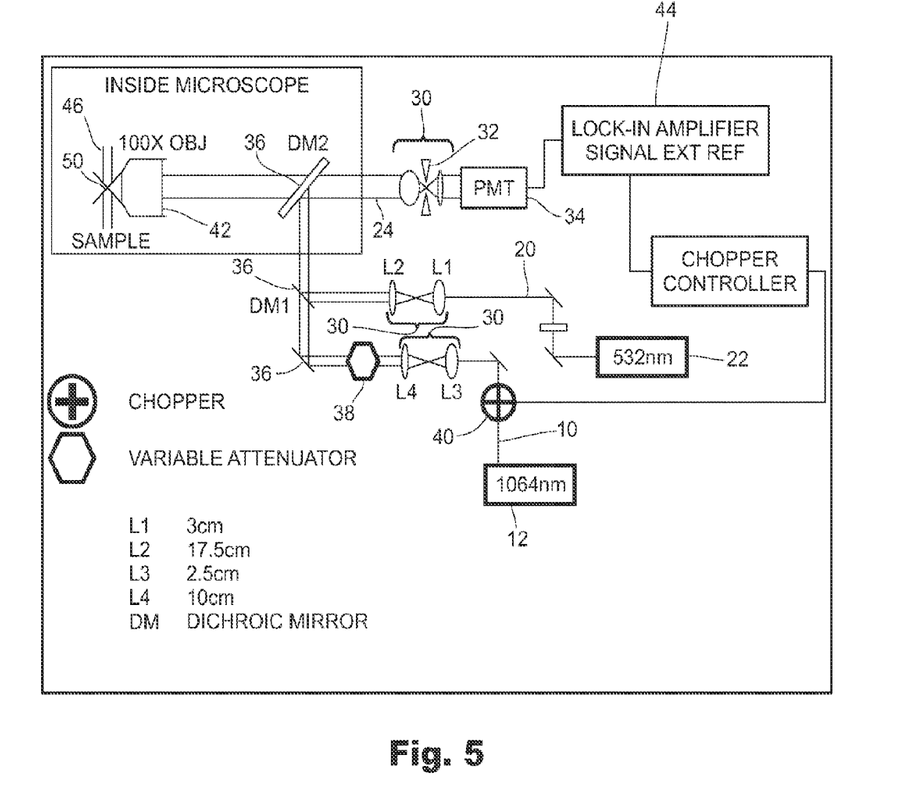

Referring to the apparatus illustrated in FIG. 5, a periodically blinking IR laser-induced increase in local particle concentration was measured with the confocal detection of the increase in the corresponding fluorescence signal in the illuminated region. Fluorescence intensity measurements with lock-in amplifier 44 were employed to improve the signal to noise ratio in order to detect the sub-thermal fluctuation level changes in local particle density induced by blinking IR laser 12. Green (532 nm) laser beam 20, aligned co-linearly with IR (1064 nm) laser beam 10, was used as the fluorescence excitation light.

Fluorescence signals 24 from the particles at common confocal point 50 of the two laser beams were collected by the same high N.A. microscope objective lens 42 that produced common focal point 50 in the sample. Fluorescence light 24 passed through pinhole aperture 32 located at a point conjugated to the common laser focus before the light was collected by photomultiplier (PMT) 34. This confocal detection scheme was employed to ensure that the detected fluorescence intensities were only from fluorescence signals 24 originating at the diffraction-limited focal region 50 (i.e., particles in the optical trap). A relationship was developed for fluorescence signal intensity vs. particle concentration, which allowed for the conversion of the changes in fluorescence intensity to changes in particle concentration, which was further converted to changes in refractive index by an independently measured dn/dC.

In an experiment to study particle-to-particle interactions using the foregoing apparatus, a suspension of fluorescent nanoparticles was prepared. The 100 nm polystyrene particles were obtained from Duke Scientific (Lot No. 31507). The stock sample was an aqueous suspension with 1% solids by weight and in a multi-component dispersing system. These particles are labeled as having excitation and absorption maxima at 542 nm and 612 nm, respectively. The samples were used without further treatments. Dilutions to prepare for other concentrations (0.25%, 0.5%, and 0.75%) were made by adding deionized water (Barnsted, Easy Pure RF). The sample chamber was a micro-capillary (Vitrocom) adhered to a microscope glass slide. Once the capillary was loaded with the sample, the ends of the capillary were sealed with high vacuum grease (Dow Corning).

The apparatus illustrated in FIG. 5 included an inverted microscope (Olympus IX-70) to measure and control particle concentrations in a colloidal suspension sample. Two co-linear laser beams were steered into the microscope from the epi-fluorescence port, where they were focused by 100× objective lens 42 (Olympus, Plan Flur) to common diffraction-limited focal point 50 in the suspension. 1064 nm IR laser 12 (Diode-Pumped Solid-State, Shanghai Dream) was used as the trapping laser, and 532 nm green laser 22 (Spectra Physics, Millemia) was used as the excitation light for detecting the fluorescent particles. Green laser 22 was attenuated to a level two to three orders of magnitude lower than the IR intensity so it would not cause photobleaching or contribute significantly to the optical trapping effect.

Before laser beams 10 and 20 were steered into the microscope, each beam was expanded with focusing optical elements 30 and collimated such that the laser beams were large enough to just overfill the back aperture of objective lens 42 and create diffraction-limited common focal point 50 in the sample. The beam expansion and collimation were achieved by passing green beam 20 through the beam expending telescope lens pair L1/L2, and the IR beam by the L3/L4 lens pair. Computer-controlled mechanical chopper 40 (Thorlabs, MC 1000A) was used to produce the periodic on-off modulation of the laser intensity at a desirable frequency. An automated neutral density filter, constructed from a neutral density filter wheel (Newport 50G00AV.2) and motorized rotation stage 46 (Tholabs CR1-Z6E) was used to vary the trapping beam power from 9.6 mW to 85 mW (measured at the exit end of objective lens 42). The automated neutral density filter wheel was controlled by a LabView program. Dichroic mirror DM1 36 (reflecting green and transmitting IR) was used to combine the two beams 10 and 20 before they were steered into the microscope. A second dichroic mirror DM2 36 (reflecting both the green and the IR, and band-passing the red fluorescence signal) was mounted in the fluorescence turret of the microscope.

Fluorescent light 24 originating from the particles in focal region 50 was collected and collimated by the same objective lens 42 mentioned above. It passed through the side port of the microscope before being focused by a 20× objective and through 25 micron pinhole aperture 32, finally reaching photomultiplier 34 (PMT, Hamamatsu 1P28A). This arrangement ensured that pinhole 32 was located at a point conjugate to the focal point of objective lens 42 in the microscope, so that only fluorescent light 24 from the particles in optical trap 50 were able to reach photodetector 34. The fluorescence intensity detected by PMT 34 was converted to an electrical current output that was fed into lock-in amplifier 44 (Stanford Research, SR-830) and into an oscilloscope (Tektronix TDS 2014-B, not shown).

The concentration of the fluorescent particles in the suspension was determined by measuring fluorescence intensity 24 of the sample under a constant intensity of green laser 20. In order to establish a relationship between the intensity of fluorescence signal 24 and the particle concentration in trap 50, fluorescence signals 24 of the sample at several different concentrations were measured in the absence of IR optical trap 50. With trapping laser 12 turned off, green laser 20 intensity was periodically (on-off) modulated by mechanical chopper 40 so that fluorescent signal 24 detected from the particles in focal region 50 varied with the chopper frequency.

To determine how IR laser 12 induced concentration changes occurred in focal region 50, the sample was simultaneously illuminated by periodically blinking IR laser 12 (at 1.8 Hz) and constant intensity green laser 22. In the presence of IR laser 12, the particles in the vicinity of focal point 50 were drawn towards the center of optical trap 50 by the optical gradient force, causing an increase in the local particle density until the concentration reached a steady state value. When IR laser 12 was blocked by chopper blade 40, the excess particles diffused out of the trap until the concentration returns to the ambient level.

Example 3

Measurement of Concentration of Suspended Pathogen (Virus) Particles

Current standard methods for pathogen, especially viral quantification based on molecular analysis are cumbersome. Existing assays require multi-step sample preparation, multiple reagents for amplification and detection, and highly skilled laboratory technicians. There is a clear opportunity to improve the overall robustness and reliability of pathogen detection assays for point of care (POC) applications, and a need exists for a portable, inexpensive and easy operating nanoparticle counter for pathogen counting usable at the point of care.

For HIV diagnostics alone, there are 30 million HIV patients worldwide needing viral load diagnosis, but have no access to the conventional test used currently due to their living in resource limited settings. The viral load tests are recommended 3-4 times a year. Despite its importance in clinical diagnosis and public health, fast and easy approaches for pathogen detection at the point-of-need are not yet available. The methods described herein may be adapted to counting whole virus particles, such as by using an optical sensor at the point of care and in any other resource-limited settings. Briefly, nanoporous membranes packaged in a microfluidic device are used to filter, concentrate and fluorescently label whole particle virions (e.g., HIV, hepatitis B, hepatitis C, influenza, and CMV). The devices are then integrated with the previously-described optical traps and detectors for processing and quantitative viral detection.

In one example, the microfluidic device (or "chip") includes nanoporous membranes to process a sample, such as virion-containing plasma. This chip contains a pre-filtration nanoporous element that separates target nanoparticles from other larger particles in the original plasma sample. The resulting purified viral suspension is then concentrated through a second membrane for mechanical nanofiltration to strain the plasma from the suspension, while retaining virions in a suspended state in a controlled small volume above the second membrane. The microfluidic viral concentrator may also be used to label target particles, such as by diffusing fluorescently labeled antibodies through either of the nanoporous membranes.

Figure 6:
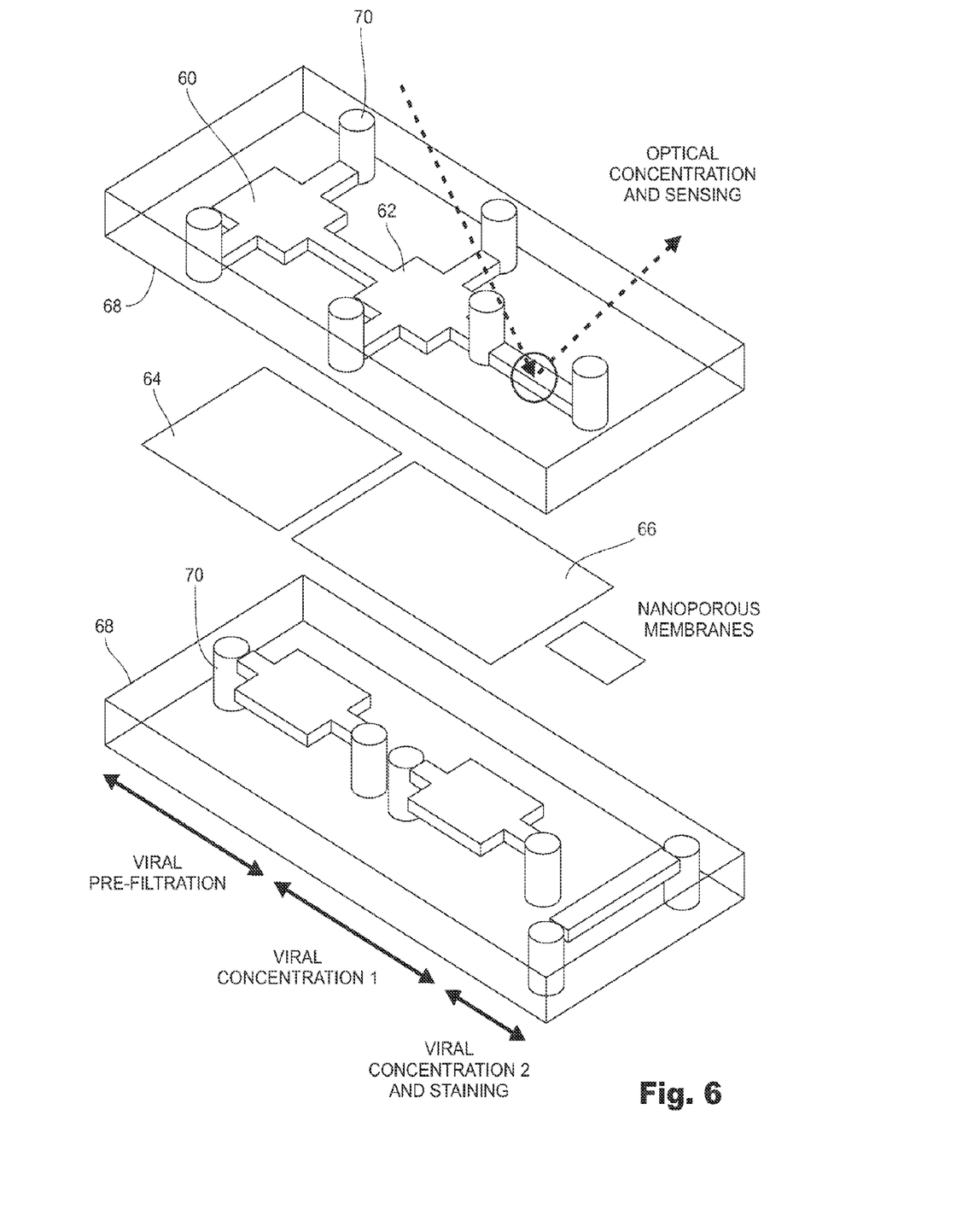
FIG. 6 schematically illustrates an exploded view of an example microfluidic cell for use in conjunction with the methods described herein.

An example microfluidic chip is illustrated in FIG. 6. Viral concentration chamber 62, which contains at least one concentration membrane 66 having pore sizes smaller than the target virions, accepts about 1 mL of pre-purified, virion-containing plasma as input from pre-filtration chamber 60, and delivers as output about 1 mL of virion suspension in the unpassaged supernatant fraction, retaining >90% input virions enriched by $10^6$ fold in about 5 min. Plasma samples are delivered into microfluidic device 68 using a pneumatic pump at a controlled pressure. In this example, microfluidic channel 70 (not all channels are labeled as such) opens a filtration area of about 0.1 cm² and membrane 64 is about 10 µm thick. This permits filtration of 1 mL plasma in less than 1 min at 5 psi pressure provided no substantial clogging occurs during plasma filtration.

To label trapped viral particles, fluorescent antibodies are diffused through concentration membrane 66 to label the target virion particles. Specific fluorescent antibodies against HIV envelope markers, such as anti-gp120, are injected into a microchannel-separated from the last stage of concentration chamber 62 by nanoporous concentration membrane 66. Antibody molecules diffuse through the nanopores to attach to and to stain the target particles. Afterwards, the antibody delivery channel is flushed with a buffer solution. The unbound antibodies in concentration chamber 66 do not respond to the optical trap due to their small size, and therefore they do not need to be eluted after labeling.

Nanoporous anodic aluminum oxide (AAO) may be used as filtration membrane 64 or concentration membrane 66, due to its excellent biocompatibility, extremely high porosity (20-50%), straight pore geometry, hydrophilicity, high flux rate, low fabrication cost and ease of processing. Additionally, the surface properties of AAO can be modified easily using silane chemistry to create desired biological functionalities. For example, in order to minimize loss from non-specific binding on the nanoporous membranes, AAO membranes may be treated with vaporized silane containing a polyethylene glycol (PEG) end group.

The size of a typical HIV virus is known to be about 90 nm to about 130 nm. By using concentrating membrane 66 of different pore sizes (illustrated in FIG. 6), concentration of the virus is controlled within the microchannel reservoir 62. Membranes of larger pore sizes (e.g., 200 nm) that are slightly larger than HIV virions separate virus particles from larger particles from the initial samples such as blood cells, cell fragments and platelets. In order to concentrate virus particles, membranes of smaller pore sizes (e.g., 20 nm) are used to enrich virus in plasma. Such membranes 64 and 66 are depicted in the exemplary chip of FIG. 6.

To assemble microfluidic chip 68, a master mold with micro-features is created by patterning a silicon substrate by deep reactive ion etching. Afterwards, a chip of PMMA, PDMS, or other suitable material is pressed onto the mold at elevated temperature to transfer the microchannel pattern. Then, two chips were clamped together with AAO membranes sandwiched in between, the microchannels 70 perpendicular to each other to define precisely an active filtration area. Afterwards, the sandwich structure is bonded together upon brief application of elevated temperature and pressure.

An optical trap and confocal fluorescence intensity detector is used to monitor trapped nanoparticles in concentration chamber 62 of microfluidic chip 68. The optical trap generated by an IR laser will further concentrate the target particles. Because the normalized change of the fluorescent intensity (ratio of the fluorescent intensity after applying the optical trap vs. before) at the focus of the optical trap is directly proportional to the initial target particle concentration, but insensitive to the absolute intensity of the particles, the intensity ratio is used to quantify viral concentration. The intensity ratio is measured by focusing a separate, visible laser beam at the center of the optical trap. The fluorescence emission light is detected confocally by a photomultiplier (PMT), as previously discussed.

An exemplary optical platform is constructed based on an inverted optical microscope. For nanoparticle enrichment, an IR laser of varying intensities is used to pull in fluorescently labeled nanoparticles into the focal region of the IR beam. Meanwhile, a green laser beam (532 nm) with much weaker intensity was aligned co-linearly with the IR (1064 nm) beam to excite the fluorescent nanobeads. Due to its weak intensity, the trapping efficiency of the green laser is negligible compared to the IR laser. The emitted fluorescence signals at the common confocal point of the two laser beams were collected confocally by a photomultiplier (PMT) (see FIG. 7).

Figure 7:
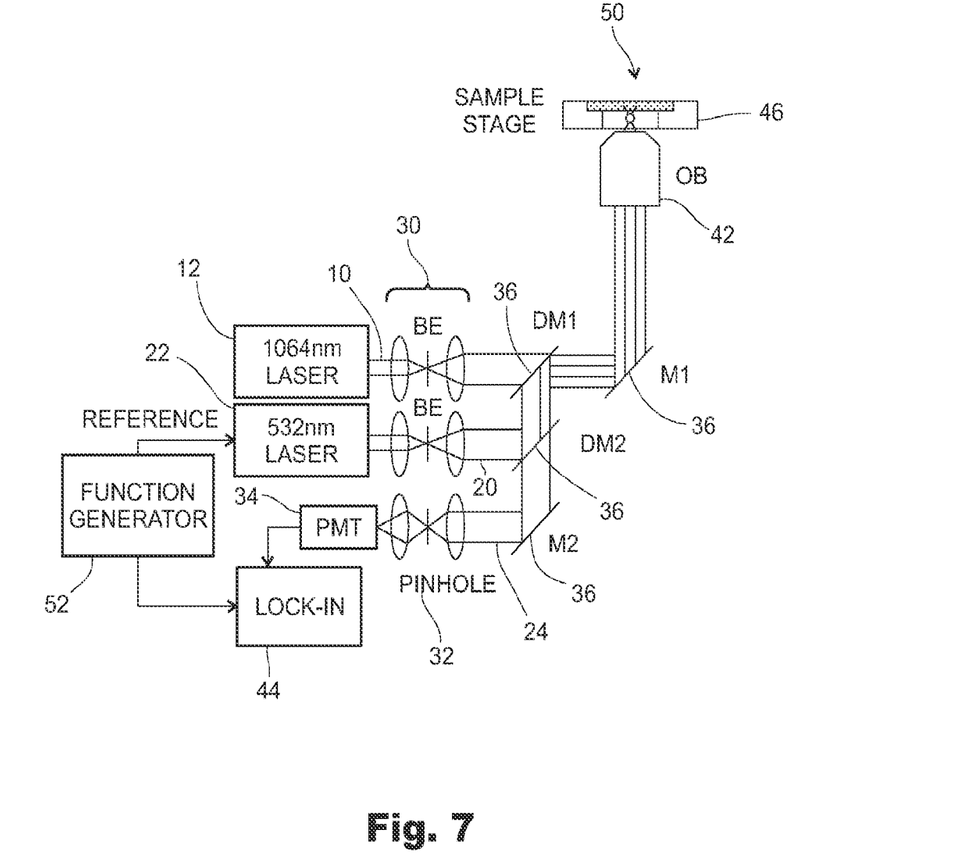

This confocal detection scheme is employed to ensure that the detected fluorescence intensities are only from the fluorescence signals originating at the diffraction-limited focal region. Fluorescence intensity measurements with a periodically chopped probe laser beam in conjunction with lock-in detection are employed to improve the signal to noise ratio in fluorescence measurement. Using such a configuration, fluorescence detection around the focal point can attract particles to the focal volume of 5 µm×5 µm×5 µm (about $10^{-10}$ mL) and the equilibrium state as monitored with a CCD camera is reached within a few seconds using a mild trapping power of about 35 mW.

Referring to the apparatus illustrated in FIG. 7, two lasers, IR laser 12 with λ of 1064 nm and maximal power of 300 mW, and visible laser 22 with λ of 532 nm and maximal power of 100 mW, are used for optical trapping and fluorescence excitation, respectively. Intensity of excitation laser 20 is attenuated to minimize its contribution to optical trapping and to minimize fluorescence photo-bleaching. Two beam expenders 30 (BE) are used to increase the laser beam size to about 8 mm so that beams 10 and 20 can slightly overfill the back aperture of high numerical aperture microscope objective lens 42 (100×, N.A. 1.30, Olympus UPlanFl). Excitation laser beam 20 and trapping laser beam 10 are combined by dichromatic mirror DM1 36 before being sent to the sample chamber through objective lens 42. Fluorescence light 24 emitted from the particles is collected by the same objective lens 42 and sent through second dichromatic mirror DM2 36. Fluorescence signal 24 originating from focal region 50 of objective lens 42 is selected by the lens-pinhole-lens assembly 32 before detection by the photomultiplier (PMT) 34. The photocurrent is analyzed by lock-in amplifier 44 with a reference signal that produces the AM modulation of trapping laser 12 intensity to enhance the signal-to-noise ratio.

The foregoing method has many advantages and improvements over art-recognized methods, devices and materials. The viral load assay herein is based on measuring intact virions in whole blood or plasma, and it eliminates the need for complex sample preparation steps of existing methods. For example, a microfluidic chip can process up to 1 mL of plasma (or, in some cases, whole blood) with an integrated optical platform that measures the concentration of intact virions in less than 30 minutes, with a detection range of 100-1,000,000 viral particles/mL, which is the clinically relevant viral load range. Additionally, whole particle detection according to our methods has reduced manual handling steps and assay time. The use of a microfluidic chip permits small reagent volume and lower operation cost, with the potential for automation and fast assay times. Moreover, the whole systems can be integrated into a portable form. Multiple types of nanoparticles may be counted in the same device by labeling them with different colors, including simultaneous detection at different wavelengths in a multiplexed assay.

While the foregoing example is described with reference to polystyrene particles and HIV virion particles and particular wavelengths of lasers, it will be understood by those skilled in the art that various changes may be made and equivalents may be substituted for elements thereof without departing from the scope. In addition, many modifications may be made to adapt a particular situation or material to the teachings hereof without departing from the essential scope. Also, in the drawings and the description, there have been disclosed exemplary embodiments and, although specific terms may have been employed, they are unless otherwise stated used in a generic and descriptive sense only and not for purposes of limitation, the scope of the claims therefore not being so limited. Moreover, one skilled in the art will appreciate that certain steps of the methods discussed herein may be sequenced in alternative order or steps may be combined. Therefore, it is intended that the appended claims not be limited to the particular embodiment disclosed herein.

The invention claimed is:

1. A method for manipulating a plurality of nanoparticles comprising: providing a first suspension of fluorescent labeled nanoparticles in a liquid solution; placing a portion of the first suspension within a reservoir; providing a first laser beam from a first laser source and a second laser beam from a second laser source; applying the first laser beam through a focusing optical element and into the reservoir to thereby establish an optical gradient and forming an optical trap within the reservoir; applying the second laser beam to the optical trap to thereby produce fluorescence optical signal from the fluorescent labeled nanoparticles within the optical trap; and detecting the fluorescence optical signal with a photodetector; and processing the detected fluorescence optical signal to determine at least one parameter selected from the group consisting of: the quantity of nanoparticles in the first suspension; the quantity of the nanoparticles in the optical trap; the concentration of nanoparticles in the first suspension; the concentration of the nanoparticles in the optical trap; the osmotic compressibility of the nanoparticles in the first suspension; and the osmotic compressibility of the nanoparticles in the optical trap.

2. The method according to claim 1, wherein the optical signal produced by the nanoparticles is correlated with the concentration of nanoparticles.

3. The method according to claim 1, wherein the optical signal produced by the nanoparticles is correlated with the magnitude of a particle-to-particle interaction.

4. The method according to claim 1, wherein a plurality of optical signals produced by the nanoparticles are measured at different intensities of the applied second laser beam.

5. The method according to claim 1, wherein second laser source is periodically interrupted to modulate application of the second laser beam at a predetermined frequency.

6. The method according to claim 1, wherein the first laser source has a wavelength in the infrared region and the second laser source has a wavelength in the visible region.

7. The method according to claim 1, wherein the nanoparticles have an average diameter smaller than the wavelengths of the first laser source and the second laser source.

8. The method according to claim 1, wherein the nanoparticles have an average diameter of between about 10 nm and about 200 nm.

9. The method according to claim 1, wherein the optical trap has a volume of about 5 $\mu m^3$ to about 100 $\mu m^3$.

10. An apparatus for manipulating a plurality of fluorescent-labeled nanoparticles in a first suspension, the apparatus comprising a first laser beam from a first laser source; a second laser beam from a second laser source; a reservoir in optical communication with the first laser source and the second laser source; a focusing optical element between the first laser source and the reservoir for establishing an optical gradient and forming an optical trap within the reservoir; and an optical detector in optical communication with the reservoir for measuring a fluorescence optical signal produced therein, the apparatus further comprising a microprocessor and computer readable instructions for processing the fluorescence optical signal to calculate at least one of the group consisting of: the quantity of nanoparticles in the first suspension; the quantity of the nanoparticle in the optical trap; the concentration of nanoparticles in the first suspension; the concentration of the nanoparticles in the optical trap; the osmotic compressibility of the nanoparticles in the first suspension; and the osmotic compressibility of the nanoparticles in the optical trap.

11. The apparatus according to claim 10, wherein the first laser source has a wavelength of about 1064 nm.

12. The apparatus according to claim 10, wherein the second laser source has a wavelength of about 532 nm.

13. The apparatus according to claim 10, wherein the optical detector is a photomultiplier tube (PMT) or charge-coupled device (CCD) camera.

14. The apparatus according to claim 10, further comprising means for periodically interrupting and modulating application of the first laser beam or the second laser beam at a predetermined frequency.

15. The apparatus according to claim 10, further comprising means for focusing the optical signal into the optical detector.

16. The apparatus according to claim 10, further comprising means for focusing the first laser beam or the second laser beam into the reservoir.

17. The apparatus according to claim 10, further comprising one or more components selected from the group consisting of light sources, confocal lenses, dichroic mirrors, beam expanders, filters, amplifiers, attenuators, and microprocessors.

18. The apparatus according to claim 10, further comprising a microfluidic device for concentrating virion particles.

19. The apparatus according to claim 18, wherein the microfluidic device comprises a filtration membrane through which virion particles freely pass and a concentration membrane that concentrates the virion particles that have passed through the filtration membrane, and wherein the microfluidic device contains an optically transparent reservoir.

* * * * *